(12) United States Patent
Browne

(10) Patent No.: US 11,752,028 B2
(45) Date of Patent: Sep. 12, 2023

(54) PNEUMATIC CERVICAL COLLAR

(71) Applicant: ATP CONCEPTS, LLC, Eagan, MN (US)

(72) Inventor: Damon Browne, Pensacola, FL (US)

(73) Assignee: ATP CONCEPTS, LLC, Eagan, MN (US)

( * ) Notice: Subject to any disclaimer, the term of this patent is extended or adjusted under 35 U.S.C. 154(b) by 29 days.

(21) Appl. No.: 16/962,463

(22) PCT Filed: Jan. 25, 2019

(86) PCT No.: PCT/US2019/015068
§ 371 (c)(1),
(2) Date: Jul. 15, 2020

(87) PCT Pub. No.: WO2019/147882
PCT Pub. Date: Aug. 1, 2019

(65) Prior Publication Data
US 2021/0077291 A1 Mar. 18, 2021

Related U.S. Application Data

(60) Provisional application No. 62/621,830, filed on Jan. 25, 2018.

(51) Int. Cl.
*A61F 5/055* (2006.01)
*A61F 5/058* (2006.01)

(52) U.S. Cl.
CPC .......... *A61F 5/055* (2013.01); *A61F 5/05816* (2013.01)

(58) Field of Classification Search
CPC .. A61F 5/055; A61F 5/05816; A61F 5/05883; A61F 5/05833; A61F 5/048; A61F 5/012; A61G 2203/723; A47C 7/36; A47C 7/38; A47C 7/383; A47G 9/10; A47G 9/1027; A47G 9/1072; A47G 9/1081
(Continued)

(56) References Cited

U.S. PATENT DOCUMENTS 3,397,688 A 8/1968 Gottfried
3,765,412 A 10/1973 Ommaya et al.
(Continued)

FOREIGN PATENT DOCUMENTS

DE 29613213 U1 * 10/1996 ............. A61F 5/012

OTHER PUBLICATIONS

DE29613213U1_original with translation.pdf.*
(Continued)

*Primary Examiner* — Keri J Nelson
(74) *Attorney, Agent, or Firm* — Christopher J. Knors; Moore & Van Allen PLLC

(57) ABSTRACT

A collar device and method of use is provided comprising a tubular structure having a longitudinal axis, the tubular structure comprising a pneumatic bottom portion configured for contouring with human shoulders; a pneumatic top portion having a first section, and a second section extending from the first section; and a plurality of pneumatic pillars each generally aligned with the longitudinal axis of the tubular structure, the plurality of pneumatic pillars each having a proximal end in proximity to the bottom portion and each having a distal end in proximity to either one of the first section or the second section of the top portion.

13 Claims, 11 Drawing Sheets

(58) Field of Classification Search
USPC .......................................................... 602/13
See application file for complete search history.

(56) References Cited

U.S. PATENT DOCUMENTS

| | | | |
|---|---|---|---|
| 4,515,153 A | 5/1985 | Calabrese | |
| 4,886,052 A | 12/1989 | Calabrese | |
| D314,623 S | 2/1991 | Calabrese et al. | |
| 5,402,535 A * | 4/1995 | Green | A41D 13/018 |
| | | | 128/DIG. 23 |
| 5,403,266 A | 4/1995 | Bragg et al. | |
| 5,752,927 A * | 5/1998 | Rogachevsky | A61F 5/012 |
| | | | 602/18 |
| 7,041,073 B1 | 5/2006 | Patron | |
| 7,048,705 B2 | 5/2006 | Pillai | |
| 7,914,472 B2 | 3/2011 | Powell et al. | |
| 8,226,698 B2 | 7/2012 | Edelman et al. | |
| 8,251,939 B2 | 8/2012 | Aune et al. | |
| D693,014 S | 11/2013 | Chiang et al. | |
| 8,734,372 B1 | 5/2014 | Graham | |
| 8,856,991 B2 * | 10/2014 | Edwards | A47C 7/383 |
| | | | 5/644 |
| 8,920,351 B2 | 12/2014 | Polliack et al. | |
| 9,289,320 B2 | 3/2016 | Hollern | |
| D754,864 S | 4/2016 | Heath | |
| 10,512,559 B2 | 12/2019 | Calco et al. | |
| D918,399 S | 5/2021 | Lou | |
| D939,094 S | 12/2021 | Papp et al. | |
| D940,338 S | 1/2022 | Alexandrescu et al. | |
| D940,961 S | 1/2022 | Heath | |
| 2002/0123706 A1 | 9/2002 | Browd | |
| 2003/0139694 A1 | 7/2003 | Rugfelt et al. | |
| 2008/0060167 A1 | 3/2008 | Hannerslag et al. | |
| 2010/0185130 A1 | 7/2010 | Rizo Patron | |
| 2013/0276213 A1 | 10/2013 | Olsson et al. | |

OTHER PUBLICATIONS

KIPO; International Preliminary Report on Patentability for International Patent Application No. PCT/US2019/015068 dated Aug. 6, 2020, 9 pages.

KIPO; International Search Report and Written Opinion for International Application No. PCT/US2019/015068 dated Apr. 25, 2019, 13 Pages.

* cited by examiner

PNEUMATIC CERVICAL COLLAR

CROSS-REFERENCE TO RELATED APPLICATIONS

This application is a 35 U.S.C. § 371 National Stage Application of International Application No. PCT/US2019/015068, filed Jan. 25, 2019, which claims the benefit of U.S. Provisional Patent Application No. 62/621,830 filed Jan. 25, 2018, the entirety of each of which is incorporated herein by reference.

TECHNICAL FIELD

The instant disclosure relates generally to cervical collar systems and more specifically it relates to a pneumatic cervical collar device. The disclosed pneumatic cervical collar device provides control of the neck and head, so that it can be maintained in a neutral position. The disclosed device avoids extension, flexion, rotation and traction during use and thus avoids applying traction to the neck.

BACKGROUND

Numerous cervical traction systems have been provided in the prior art that are adapted to provide therapeutic supports for people having injured necks. While these units may be suitable for the particular purpose to which they address, they would not be as suitable for the purposes of the present disclosure as heretofore described.

SUMMARY

In a first embodiment, a collar device is provided, the device comprising: a tubular structure having a longitudinal axis, the tubular structure comprising: a pneumatic bottom portion configured for contouring with human shoulders; a pneumatic top portion having a first section and a second section extending from the first section; and a plurality of struts each generally aligned with the longitudinal axis of the tubular structure, the plurality of struts each having a proximal end in proximity to the bottom portion and each having a distal end in proximity to either one of the first section or the second section of the top portion.

In a second embodiment, a collar device is provided, the device comprising: a tubular structure having a longitudinal axis, the tubular structure comprising: a pneumatic bottom portion, the bottom portion having a generally hollow cylindrical shape (or ring or annulus or annular cylinder or oval annulus) configured for contouring with at least a portion of a human's shoulders; a pneumatic top portion, the top portion having a generally hollow cylindrical shape (or ring or annulus or annular cylinder or oval annulus) having a first section configured for contouring with at least a portion of a human mandible and a second section extending from the first section for contouring with at least a portion of a human's occiput; and a plurality of struts each generally aligned with the longitudinal axis of the tubular structure, the plurality of struts each having a proximal end in proximity to the bottom portion and each having a distal end in proximity to either one of the first section or the second section of the top portion.

In a third embodiment, a collar device is provided, the device comprising: a tubular structure having a longitudinal axis, the tubular structure comprising: a ring-shaped pneumatic bottom portion configured for contouring with at least a portion of human shoulders; a ring-shaped pneumatic top portion having a first section configured for contouring with at least a portion of a human mandible and a second section extending from the first section for contouring with at least a portion of a human occiput; and a plurality of struts each generally aligned with the longitudinal axis of the tubular structure, the plurality of struts each having a proximal end in proximity to the bottom portion and each having a distal end in proximity to either one of the first section or the second section of the top portion.

The present device allows independent control of the forward and backward tilt of the head (flexion/extension) to eliminate compression and irritation of the articular cartilage of the anterior and posterior cervical spine joints and cervical spinal cord, and of the temporomandibular (jaw) joints.

The present device provides a pneumatic cervical collar device that is lightweight and compactable, and is simple and easy to use and economical in cost to manufacture.

The novel features which are considered characteristic for the disclosure are set forth in the appended claims. The disclosure of the present device, both as to its construction and its method of operation, together with advantages thereof, will be best understood from the following description of the embodiments when read in combination with the accompanying drawings.

BRIEF DESCRIPTION OF THE DRAWINGS

The advantages and characterizing features of the present disclosure will become apparent from the following description of certain illustrative embodiments. However, the drawings are illustrative only, and that changes may be made in the specific construction illustrated and described within the scope of the appended claims. Various other objects, features and advantages of the present disclosure will become apparent as when considered in conjunction with the accompanying drawings, in which like reference characters designate the same or similar parts throughout the several views.

DETAILED DESCRIPTION

Figure 1A:
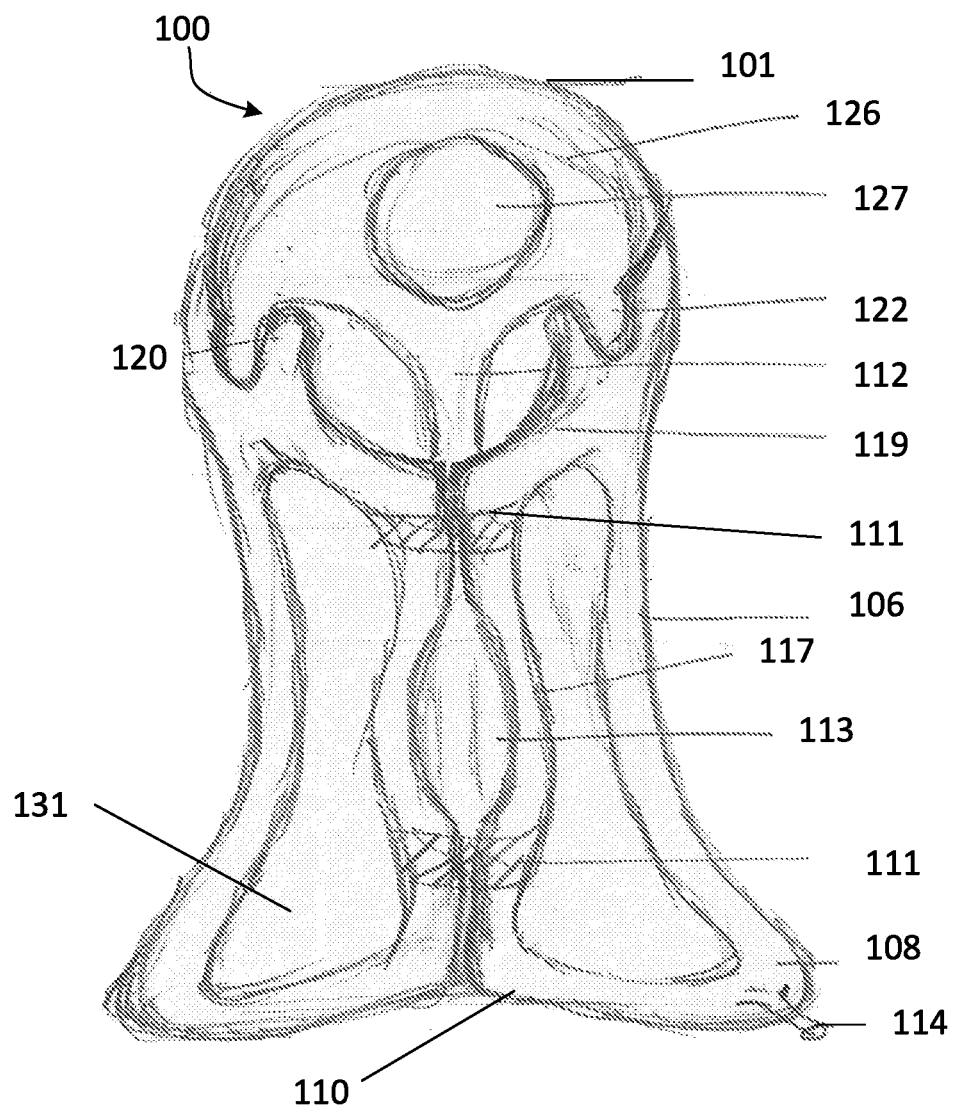
FIGS. 1A and 1B are anterior and partial lateral perspective views, respectively, of an embodiment of the device disclosed and described herein.
Figure 1B:
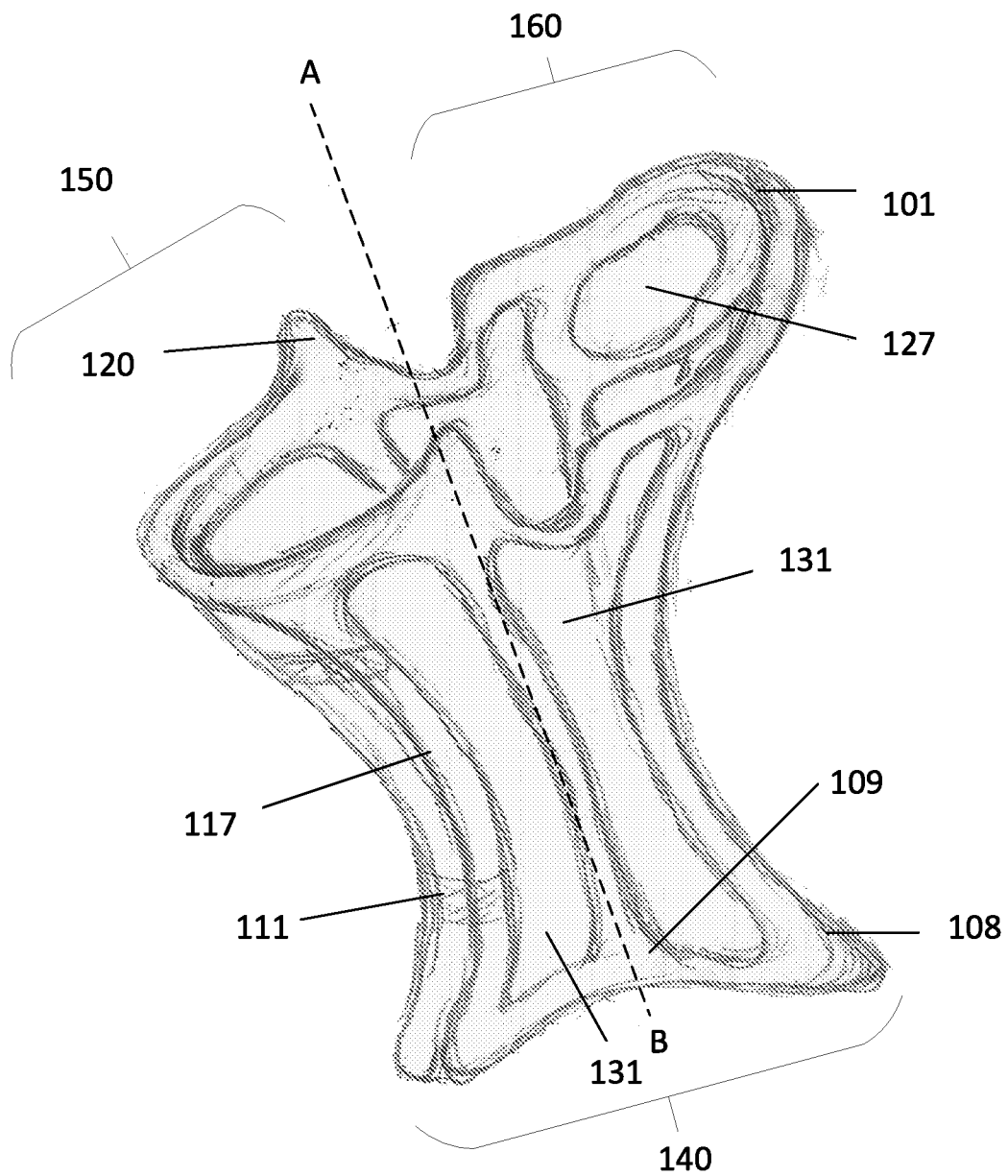

When used herein, terms such as "vertical", and "axial" or "horizontal" generally are in relation to a defined longitudinal axis, and if no such longitudinal axis is specifically defined, a longitudinal axis corresponding to that of a human body it is intended by default.

When used herein, terms such as "lateral", "anterior", and "posterior" are inclusive of their generally accepted definitions as used in the medical field.

The present disclosure is concerned with a pneumatic cervical collar device. The device generally presents a tubular structure consisting of a plurality of inflatable pillars each generally aligned with the longitudinal axis A-B of the tubular structure to correspond with the posterior, anterior, and lateral sides of the human head and neck, the plurality of inflatable pillars each having a proximal end in proximity to a bottom portion (i.e., clavicular buttress) configured to engage shoulders of a subject, and each having a distal end in proximity to either one of a first section or a second section of a top portion (i.e., mandibular/occiput buttress) the top portion configured to receive and engage a jaw and head regions of the subject.

Each of the inflatable pillars has at least one inflatable chamber. In one example, the pneumatic pillars are integral with non-pneumatic struts. In another example, one or more pneumatic pillars are independently configured to receive a non-pneumatic strut, either during assembly or prior to use. The non-inflatable strut provides structural rigidity to the device and assists in maintaining the subject's head and neck in a fixed position.

The device comprises a valve or functional equivalent for connecting to an air or gas delivering device. In one example, the valve is one way for retaining the air delivered to the device. In another example, the valve of the device also functions to release the air delivered to the device or deflation, removal, and storage of the device. The air or gas delivery device can be, for example, via a handheld pump, a sphygmomanometer-type bulb, or can be a foot-operated air pump or a powered pump, a chemical-gas generating system, or a simple tube for manually inflating by mouth. In one example, air or gas is inclusive of oxygen, nitrogen, and carbon dioxide in any relation or proportion. In one example, water infusion can be used as a replacement for gas, for example, air transport of a subject while using the device, so as to mitigate gas pressure changes during flight.

With regard to the inflating means, in one example, the device includes a single inflation port. In another example, the device includes at least two inflation ports, a first inflation port, for example, located on the front portion of the clavicle pneumatic buttress, and a second inflation port, for example, located on the rear portion of the occiput rim. For releasing the air in the inflated device, for example, when removing the device, the chambers are deflated, for example, via a quick-release open/close valve integral with each port. The device may further comprise a pressure gauge. The pressure gauge can be coupled to the air delivering device or positioned on or integral with the device.

In one example, the plurality of pneumatic pillars comprises interconnected, pneumatic chambers. In another example, the interconnected, pneumatic chambers are configured with partitioned chambers containing separated and independently pneumatically accessible sections; means for separately inflating the sections; and means for separately deflating the sections. In one example, the interconnected pneumatically accessible chambers are dimensioned with different internal diameters, different wall thicknesses, and/ or comprise independent flow regulating valves for selectively controlling distribution of the volume of air introduced by the air delivering device. For example, one wave flow regulating valves having different sized orifices may be employed to selectively inflate one section at a rate greater than inflation of another section within the interconnected pneumatic chambers.

In one example, the device of the present disclosure will contain from 3 to 9 of the vertically aligned pneumatic pillars and 2 horizontal buttresses. In another example, the device of the present disclosure will contain 9 vertically aligned pneumatic pillars and 2 horizontal buttresses.

In one example, the horizontal pneumatic buttresses are stabilized by a matrix of medical quality material, such as a vinyl resin or vinyl polymer, and are securely attached to the pneumatic components in an arrangement that provides open spaces that will permit aeration, drainage, or drying, as well as visual access to the underlying anatomy; this matrix will permit ease of application as the device will be applied in a wraparound manner then inflated.

In one example, the axial (vertically aligned) struts are encased in a tube and are secured at the top ends at manufacture, or are configured to be inserted and/or replaced prior to or after use.

In one example, the device is configured to prevent or inhibit vertical expansion and/or vertical stretching (relative to the longitudinal axis) of the pillars and buttress components so as to avoid or eliminate neck extension. In another example, the device is configured to prevent expansion and/or stretching of the components so as to eliminate neck extension.

In another example, the device is configured for efficient and convenient folding that accommodates the mandibular struts and axial struts.

In one example, the device is configured to eliminate the need to inflate with liquid, such as saline or water.

In one example, the device is configured where one or more of the axial struts are non-pneumatic. In another example, the device is configured where all of the axial struts are non-pneumatic. In one example, the struts comprise a flexible but rigid material, such as plastic, wood, resin, composites, or metal. In one example, the device is substantially free of radio-opaque material. In another example, the device is radiological neutral so as to permit visualization of anatomy with conventional medical diagnosis equipment used to exam the neck and head area of a subject.

In one example, at least a portion of the device is constructed from non-brittle material, such as an elastomeric material or other flexible material. In another example, the device is constructed from an at least partially expandable, elastomeric material of a durometer hardness of 0 to 60, or the equivalent, so as to provide supplemental axial stability and/or provide support with or without inflation. In one example, the device can be fabricated from the group of low durometer plastics, such as SANTOPRENE®, non-latex rubber and/or similar natural and synthetic substances, polyvinyl chloride (PVC), silicone, and polyurethane. In one example, the device is constructed of a hypoallergenic material.

In one example, one or more of the plurality of pneumatic pillars that house either the axial and mandibular struts comprise inserts or pouches that can be sealed upon receiving the strut. In another example, one or more of the plurality of pillars that house the axial and mandibular struts comprise inserts or pouches that are not pneumatic, for example, are molded and closely fitting of the circumference or outer dimension of the struts and are sealed at manufacture to prevent displacement of the struts during actuation or inflation of the device.

In one example, a function of the axial and mandibular struts is to impart supplemental axial and mandibular stability to one or more areas of the device. In another example, a function of the axial and mandibular struts is to impart supplemental axial and mandibular stability to one or more areas of the device with or without inflation. In yet another example, a function of the axial and mandibular struts is to impart supplemental axial and mandibular stability to one or more areas of the device as a fail-safe or fall-back function of stabilizing the traumatized neck in the event of unintended deflation or should pneumatic inflation fail. While neck flexion, rotation, traction or extension of a subject in need of the device herein described is to be avoided, it should be understood that in at least one configuration of the device, avoidance of neck extension, flexion, rotation, traction is not the intended purpose or function of the struts.

In one example, the device is configured such that any lateral or tangential migration of one or more of the pneumatic buttresses will be contained or prevented from collapse by the combination of pneumatic pillars and buttresses. In another example, the device is configured such that any lateral or tangential migration of one or more of the pneumatic buttresses will be contained or prevented from collapse by the combination of pneumatic pillars and buttresses alone or in combination with brace elements tethered horizontally to two or more of the pillars.

In one example, a single inflation/filling port is provided. In another example, a plurality of inflation/filling ports are provided. In yet another example, separate ports and inflation-limitations within the pneumatic circuit are employed, for example, to isolate the occiput cushion so as to inflate the occiput cushion at a greater pressure to receive the weight of the patient's head.

The device can include or contain a facility for introducing air into the plurality of pneumatic pillars of the collar to inflate each of the pillars at various pressurized amounts, so that the collar can properly and adjustably support the neck of the person. The device can further include an assembly for releasing air from the plurality of pneumatic pillars of the collar, so that the collar can deflate to be easily removed from the neck of the person or for storage.

One or more sets of hook and loop type fasteners (for example, VELCRO®), attached to one or more of the inflatable pillars can be provided for securing the pillars in spaced apart positions in a releasable manner. Other fastening means may be used.

Turning now descriptively to the drawings, in which similar reference characters denote similar elements throughout the several views, FIGS. 1 through 5 illustrate a pneumatic cervical collar device 100, 200, 300, 400 and 500. With reference to FIGS. 1A and 1B, device 100 is shown comprising a generally tubular structure, having a longitudinal axis A-B, the tubular structure comprising a ring-shaped pneumatic bottom portion 140; a ring-shaped pneumatic top portion having a first section 150 and a second section 160 extending from the first section. Ring-shaped is intended to be inclusive of an oval shape as well as a round shape and combinations thereof. When viewed along the longitudinal axis A-B, the ring-shaped portions can be concave or convex so as to provide the intended function of interacting with the anatomy of the subject.

In one example, as shown in FIG. 1A, device 100 comprises a plurality of anterior, lateral, and posterior pneumatic pillars 106, 109, and 117, at least one of which is configured to receive a non-pneumatic strut (not shown). Each of the plurality of pneumatic pillars are generally aligned with the longitudinal axis A-B of the tubular structure. The plurality of pneumatic pillars terminate at one end in posterior clavicular pneumatic buttress 108, or lateral clavicular pneumatic buttress 109, or anterior clavicular pneumatic buttress 110. Posterior clavicular pneumatic buttress 108, lateral clavicular pneumatic buttress 109, and anterior clavicular pneumatic buttress 110 are configured for contouring with at least a portion of human shoulders. The plurality of pneumatic pillars terminate (or transition into) at their respective other ends either at mandibular pneumatic buttresses 119 of first section 150 and are configured for contouring with at least a portion of a human mandible, and posterior axial pneumatic buttress 112 of second section 160 and are configured for contouring with at least a portion of a human occiput. As shown, first section 150 includes pre-auricular extensions 120 that provides recesses 122 for allowing the subject's ears to reside outside of the device. As shown, second section 160 includes occiput cushion 127 positioned posteriorly within occiput rim 101 and optionally contains a cotton or absorbent fabric 126.

Figure 2A:
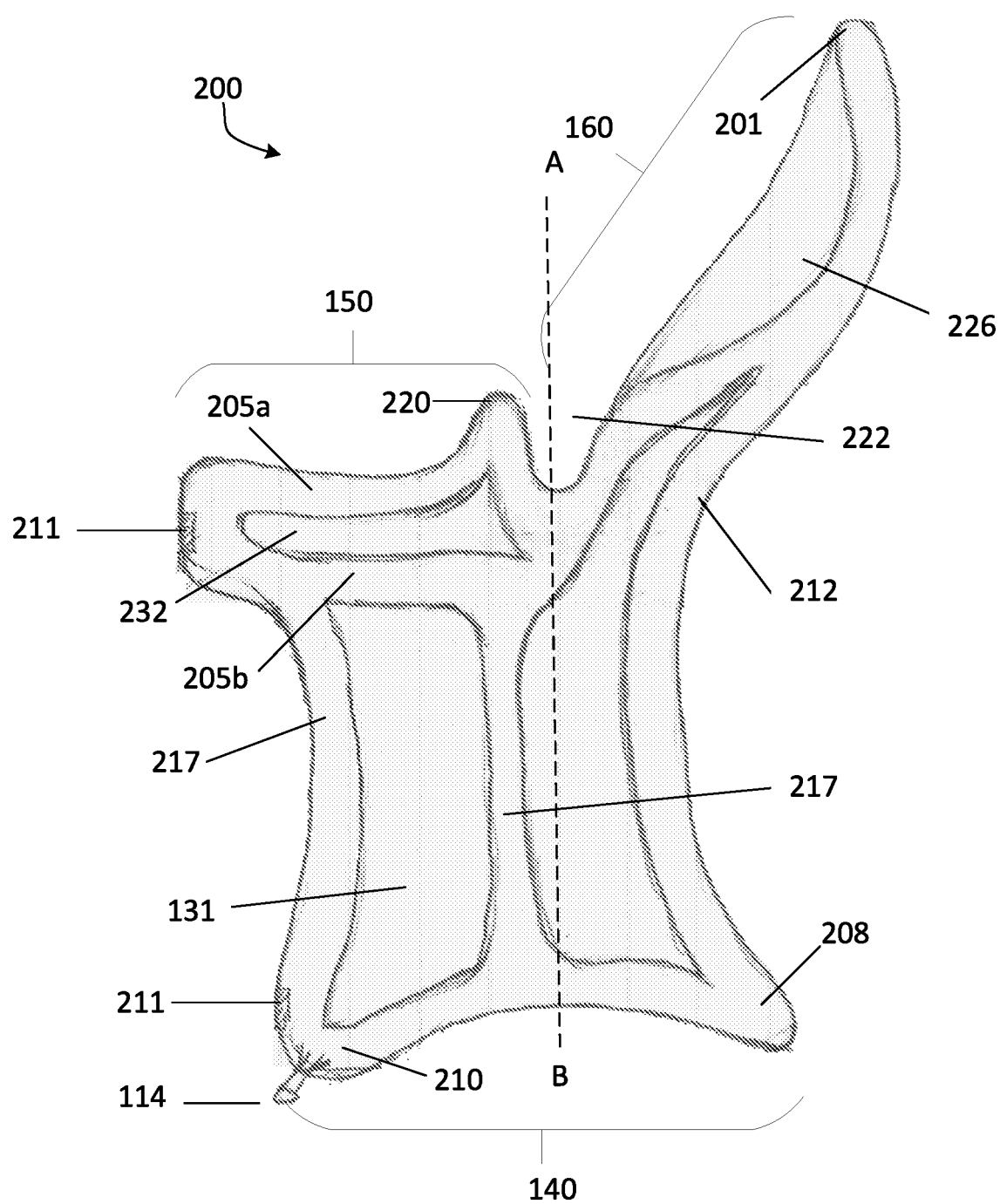
FIGS. 2A and 2B are lateral and anterior perspective views, respectively, of an alternate embodiment of the device disclosed and described herein.
Figure 2B:
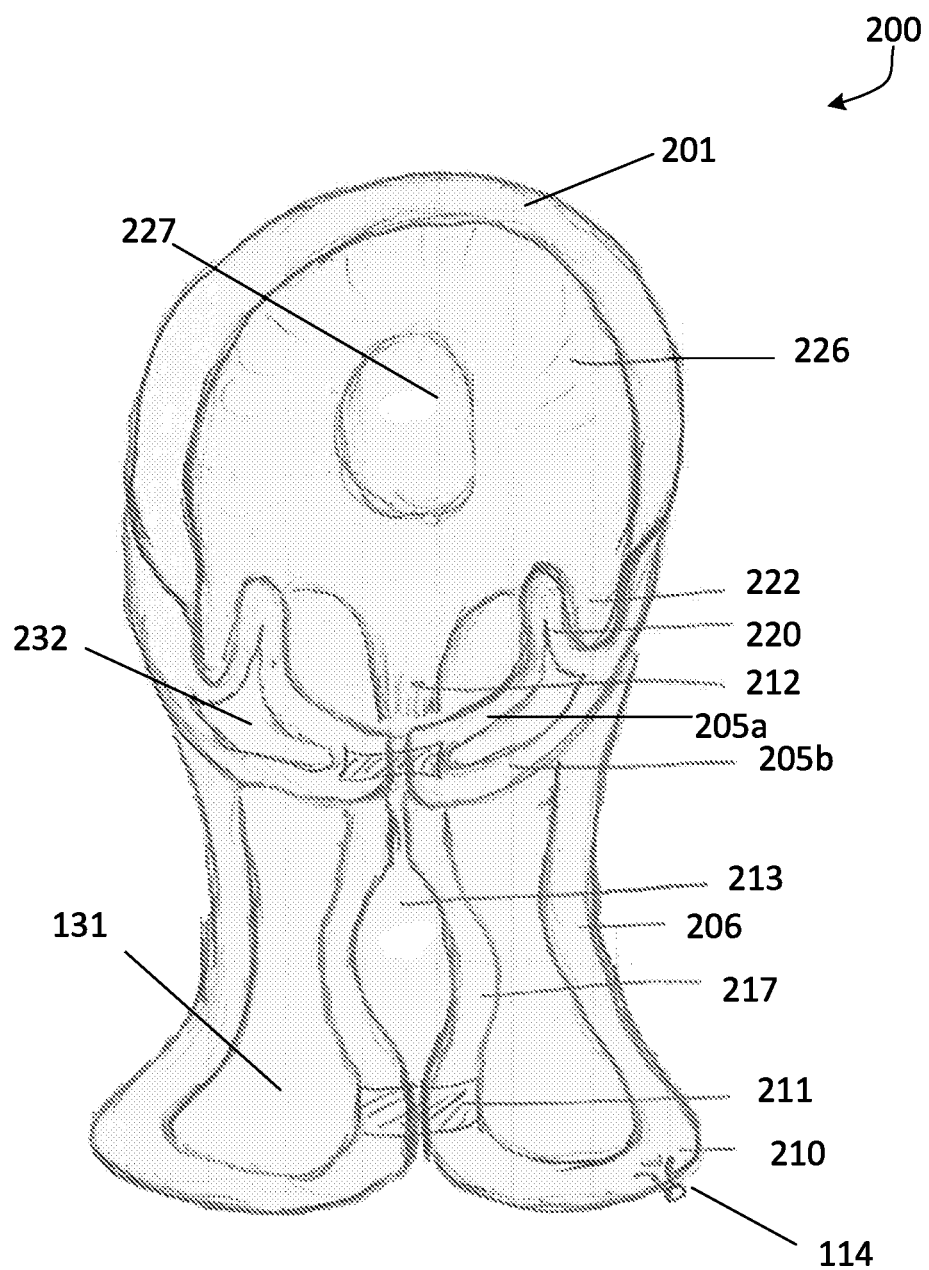
Figure 3A:
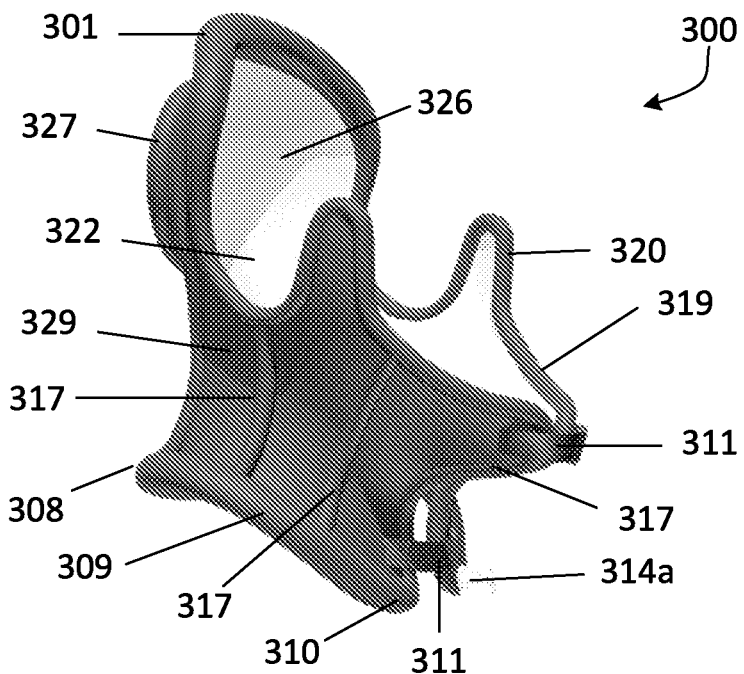
FIGS. 3A, 3B, and 3C are partial lateral, anterior, and posterior perspective views, respectively, of an alternate embodiment of the device disclosed and described herein.
Figure 3B:
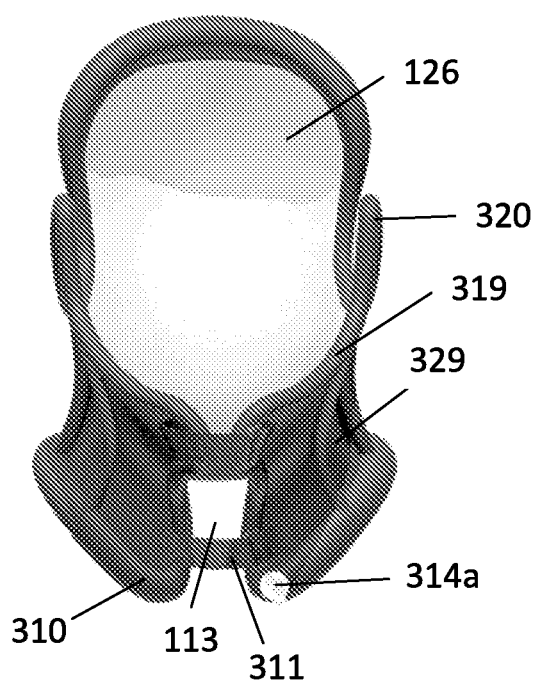
Figure 3C:
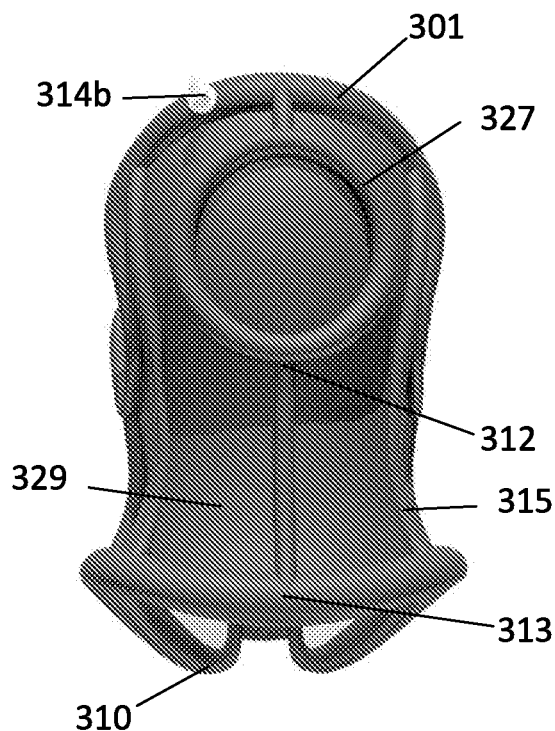
Figure 3D:
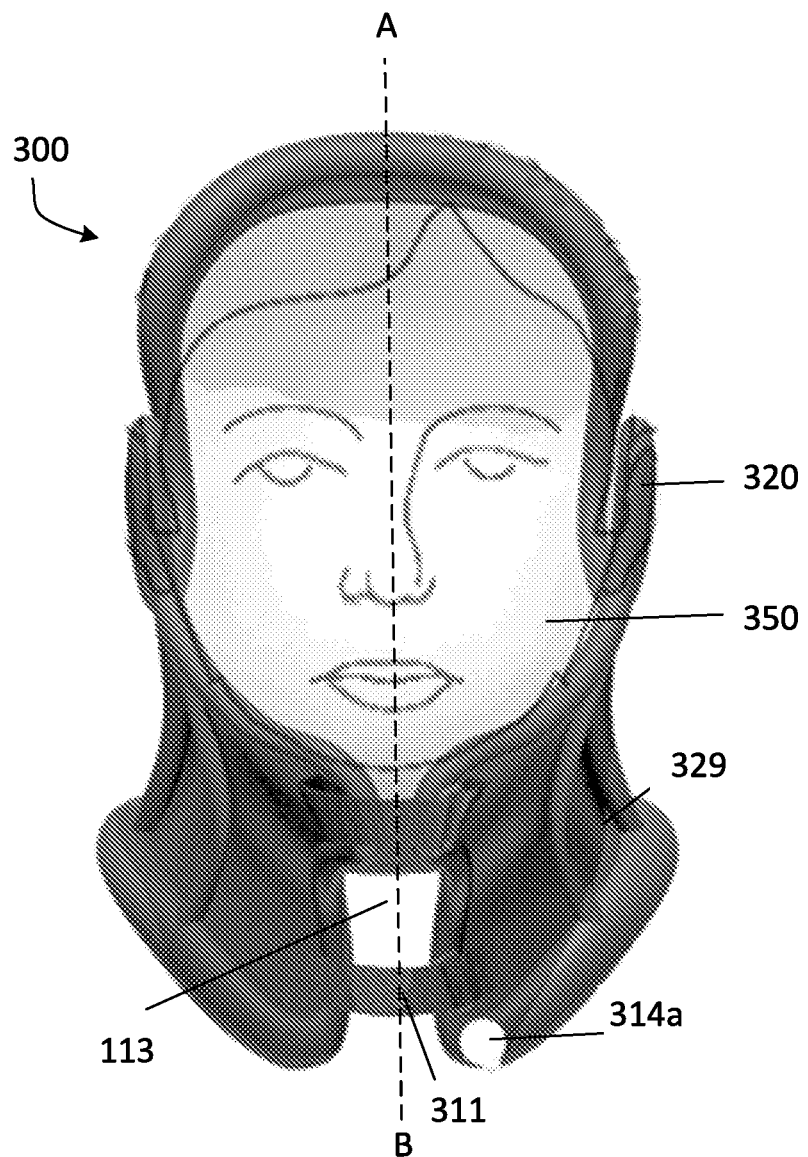
FIG. 3D is an anterior perspective view of the device of FIG. 3 shown in use.

Still referencing FIGS. 1A and 2B, the plurality of pneumatic pillars 106, 109, and 117, provide for openings 131 with the advantage of reducing the overall weight of the device, cost of manufacture, and providing ample air circulation during use. In addition, a pair of pneumatic pillars 117 provide a curved aperture 113. Curved aperture 113 provides for a surgical passageway or thyroid/cricoid access without necessitating the removal of the device. In one example, one or more sets of fasteners 111, attached to adjacent inflatable pillars are provided for securing the pillars in spaced apart positions in a releasable manner.

Using the device would require separation of the fasteners 111 coupled to the pair of anterior cervical pillars 117, for example, and positioning the device about the subject's head and neck area such that the plurality of pillars are generally aligned with the longitudinal axis of the subject. Fastening of the fasteners 111 with at least partial inflation via inflation port 114 secures the device to the subject's head and neck area. Deflation of the device and/or opening of fasteners 111 provides for removal of the device from the subject.

An exemplary additional embodiment of the present disclosure is shown with reference to FIGS. 2A and 2B. Device 200 also comprises a generally tubular structure, having a longitudinal axis A-B, the tubular structure comprising a ring-shaped pneumatic bottom portion 140; a ring-shaped pneumatic top portion having a first section 150 and a second section 160 extending from the first section as previously described for device 100.

As shown in FIGS. 2A and 2B, device 200 also comprises a plurality of pneumatic pillars 206, 209, and 217, at least one of which is configured to receive a non-pneumatic strut (not shown). Each of the plurality of pneumatic pillars are generally aligned with the longitudinal axis A-B of the tubular structure. The plurality of pneumatic pillars terminate at one end in posterior clavicular pneumatic buttress 208, or lateral clavicular pneumatic buttress 209, or anterior clavicular pneumatic buttress 210. Posterior clavicular pneumatic buttress 208, lateral clavicular pneumatic buttress 209, and anterior clavicular pneumatic buttress 210 are configured for contouring with at least a portion of human shoulders. The plurality of pneumatic pillars terminate (or transition into) at their respective other ends at mandibular pneumatic buttresses 205b of first section 150 and are configured for contouring with at least a portion of a human mandible, and posterior axial pneumatic buttress 212 of second section 160 and are configured for contouring with at least a portion of a human occiput. As shown, first section 150 includes pre-auricular extension 220 that provides recesses 222 for allowing the subject's ears to reside outside of the device. As shown, second section 160 includes occiput cushion 226 with occiput recess 227 positioned within occiput rim 201 and optionally contains a cotton or absorbent fabric.

Still referencing FIGS. 2A and 2B, the plurality of pneumatic pillars 206, 209, and 217, provide for openings 231 as well as openings 232 provided by horizontal buttresses 205a, 205b of first section 150, with the advantage of reducing the overall weight of the device, cost of manufacture, and providing ample air circulation during use. In addition, a pair of pneumatic pillars 217 provide a curved aperture 213, where curved aperture 213 provides for a surgical airway without necessitating the removal of the device. In one example, one or more sets fasteners 211, attached to adjacent inflatable pillars are provided for securing the pillars in spaced apart positions in a releasable manner.

In one example, the device is dimensioned for adults. As shown in FIGS. 2A and 2B, an acceptable adult dimension are as follows: length C of the chin/mandible buttresses 205a, 205b region can be 1-2 inches (2.54-5.08 centimeters), lateral width D) can be 11-13 inches (27.9-33.0 centimeters), the clavicular extension region-to-chin/mandible buttress height E can be 6-8 inches (15.2-20.3 centimeters), occiput cushion-from-pre-auricular extension height F can be 6-8 inches (15.2-20.3 centimeters), the width G of the occiput cushion can be 9-11 inches (22.9-27.9 centimeters), and the width H of the clavicular extension can be 11-13 inches (27.9-33.0 centimeters), In another example, the device is dimensioned for juveniles or pediatric subjects, with the aforementioned dimensions being appropriately adjusted. In another example, the device can be color coded and/or fluorescently numbered for low light conditions, for facilitating proper size selection during use.

With reference now to FIGS. 3A, 3B, 3C and 3D, and additional exemplary device 300 is shown. Device 300 is similar to that of device 100 but for the absence of openings/spaces between the pneumatic pillars. Thus, device 300 comprises a plurality of pneumatic pillars 306, 309, 315, and 317, at least one of which is configured to receive a non-pneumatic strut (not shown). Each of the plurality of pneumatic pillars are generally aligned with the longitudinal axis A-B of the tubular structure. The plurality of pneumatic pillars terminate at one end in posterior clavicular pneumatic buttress 308, or lateral clavicular pneumatic buttress 309, or anterior clavicular pneumatic buttress 310. Posterior clavicular pneumatic buttress 308, lateral clavicular pneumatic buttress 309, and anterior clavicular pneumatic buttress 310 are configured for contouring with at least a portion of human shoulders. The plurality of pneumatic pillars terminate (or transition into) at their respective other ends either at mandibular pneumatic buttresses 319 and are configured for contouring with at least a portion of a human mandible, and posterior axial pneumatic buttress 312 and are configured for contouring with at least a portion of a human occiput. As shown, occiput cushion 327 is operably connected to posterior axial pneumatic buttress 312 and then continues to occiput rim 301. As shown, first section 150 includes pre-auricular extension 320 that provides recesses 322 for allowing the subject's ears to reside outside of the device. As shown, second section 160 includes occiput cushion positioned posteriorly within occiput rim 301 and optionally contains a cotton or absorbent fabric 326.

Still referencing FIGS. 3A-D, the plurality of pneumatic pillars 306, 309, and 317 are integrated with fabric 329, preferably a breathable fabric, with the advantage of improving the axial stability of the device, cost of manufacture, whilst providing ample air circulation during use. In addition, a pair of pneumatic pillars 317 provide a curved aperture 313, where curved aperture 313 provides for a surgical airway to subject 350 without necessitating the removal of the device. In one example, one or more sets fasteners 311, attached to adjacent inflatable pillars are provided for securing the pillars in spaced apart positions in a releasable manner. Inflation of device 300 can be via inflation ports 314a, 314b With reference to FIGS. 4A, 4B, and 4C, another exemplary additional embodiment of the present disclosure is shown as device 400. Device 400 also comprises a generally tubular structure, having a longitudinal axis A-B, the tubular structure comprising a ring-shaped pneumatic bottom portion 140 with lateral clavicular pneumatic buttress 409 and posterior axial pneumatic buttress 421; a ring-shaped pneumatic top portion having a first section 150 and a second section 160 extending from the first section as previously described for device 100.

Figure 4A:
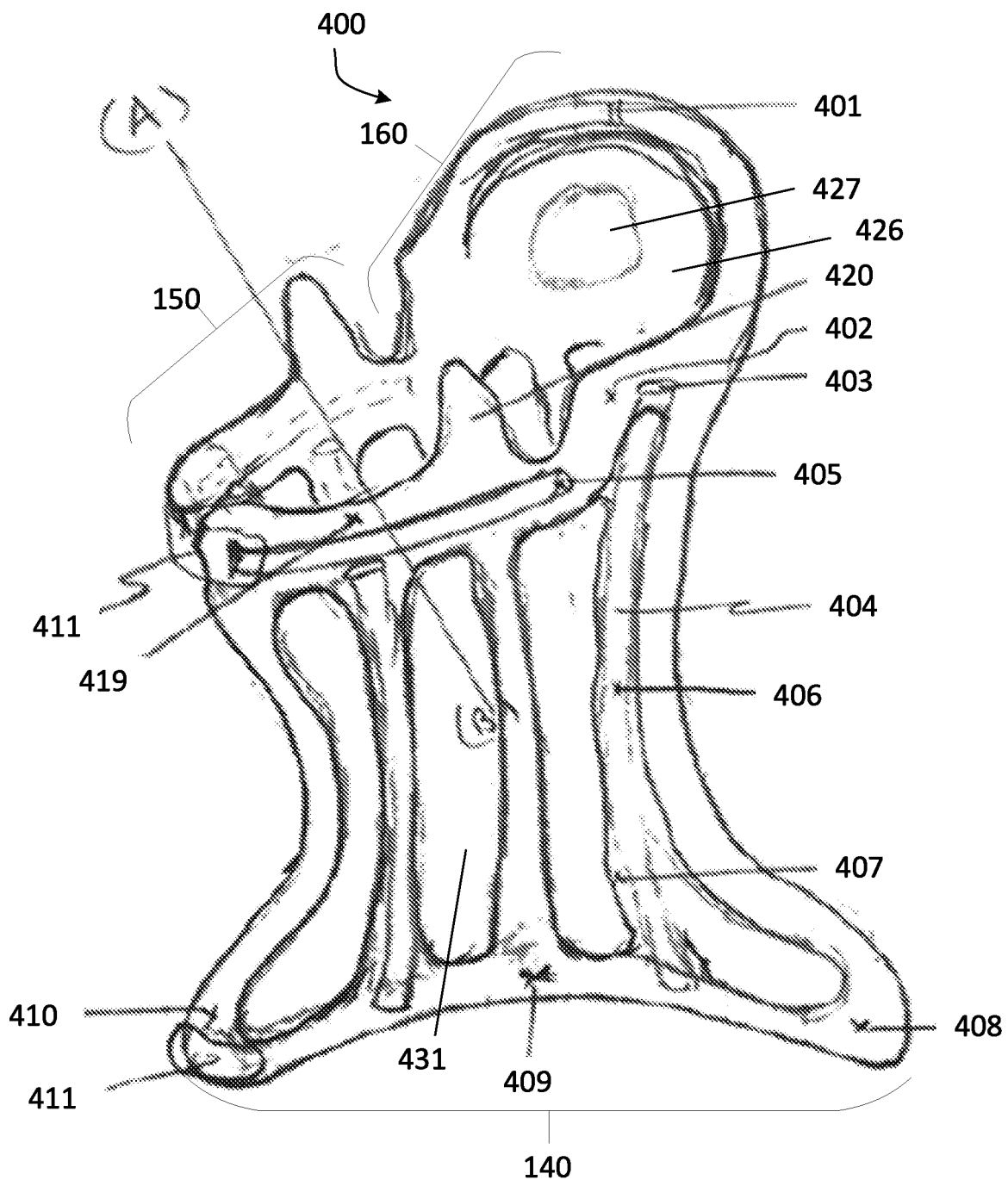
FIGS. 4A, 4B, and 4C are partial lateral, anterior, and posterior perspective views, respectively, of an alternate embodiment of the device disclosed and described herein.
Figure 4B:
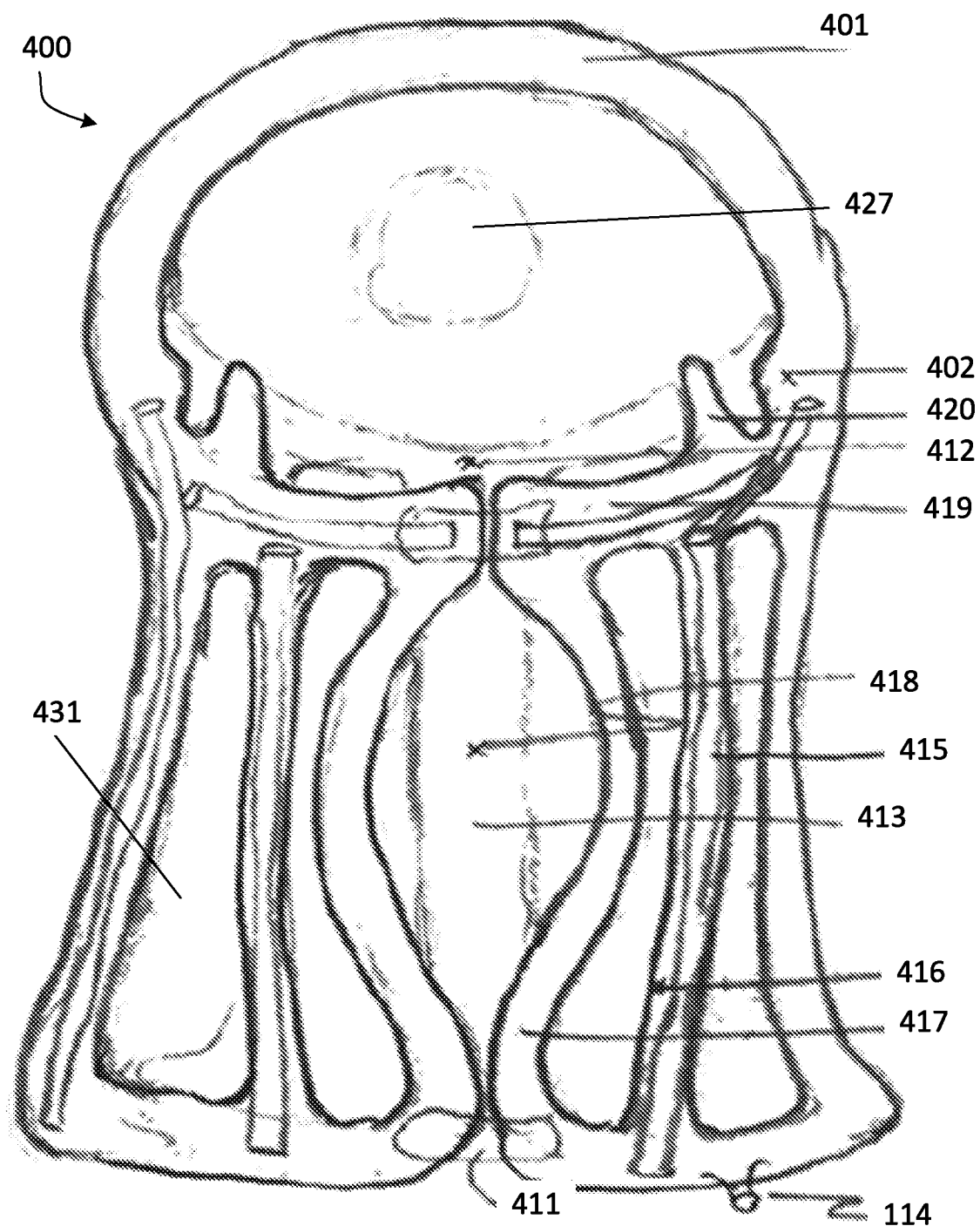
Figure 4C:
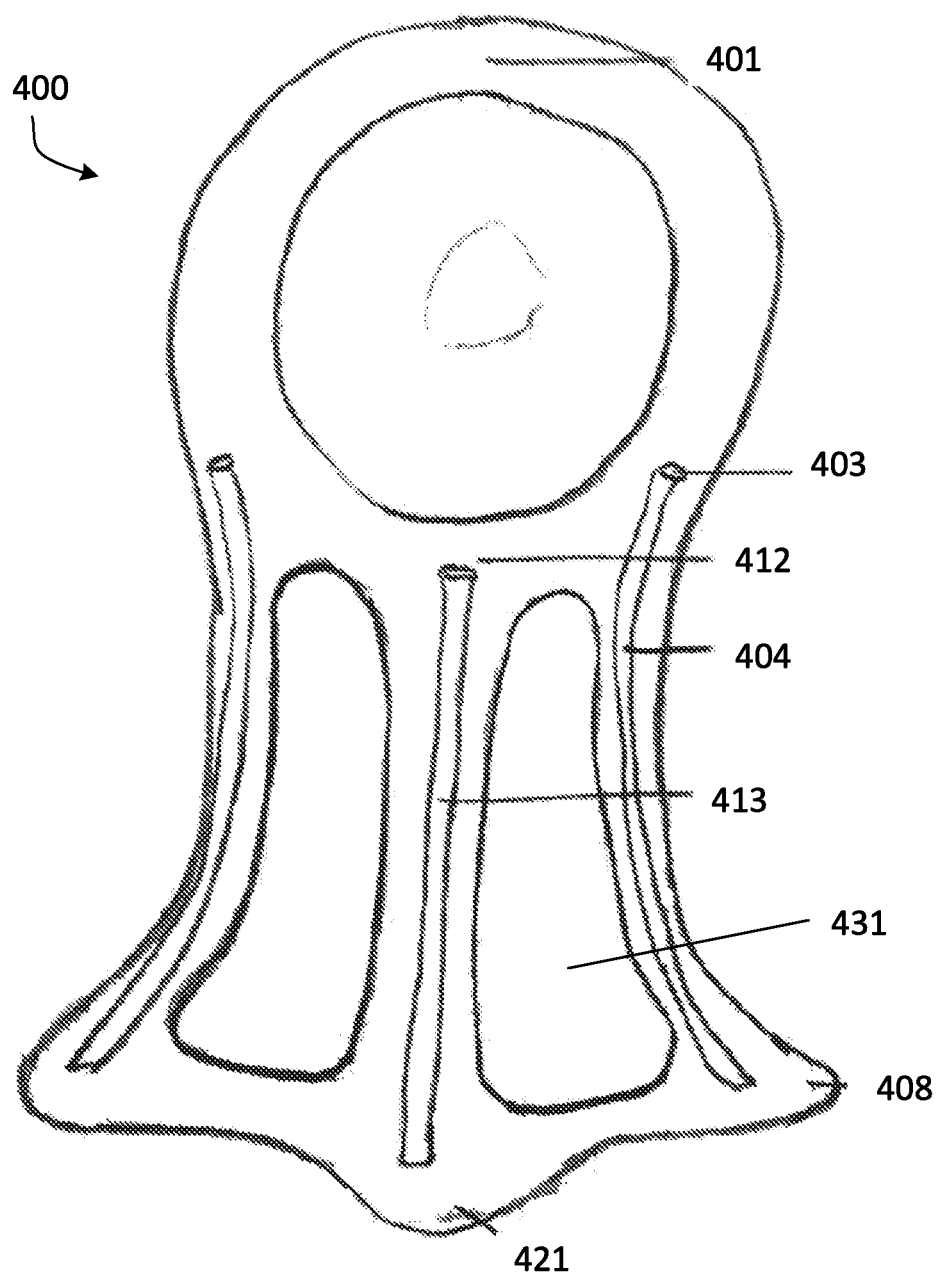

As shown in FIGS. 4A-C, device 400 comprises a plurality of pneumatic pillars, 404, 407, and 416, fillable via inflation port 114, at least one of which is shown configured to receive axial non-pneumatic struts 406, 415 via opening 403. In one example, the non-pneumatic struts 406, 415 are arranged with pneumatic pillars 404 and 416, respectively, without a non-pneumatic strut positioned there between, as shown. In another example, the non-pneumatic struts 406, 415 are arranged in each pneumatic pillar. Each of the plurality of pneumatic pillars are generally aligned with the longitudinal axis A-B of the tubular structure. The plurality of pneumatic pillars terminate at one end in posterior clavicular pneumatic buttress 408, or lateral clavicular pneumatic buttress 409, or anterior clavicular pneumatic buttress 410. Posterior clavicular pneumatic buttress 408, lateral clavicular pneumatic buttress 409, and anterior clavicular pneumatic buttress 410 are configured for contouring with at least a portion of human shoulders. The plurality of pneumatic pillars terminate (or transition into) at their respective other ends either at mandibular pneumatic buttresses 419 (shown with lateral non-pneumatic strut 405) of first section 150 and are configured for contouring with at least a portion of a human mandible, and posterior axial pneumatic buttress 418 of second section 160 is configured for contouring with at least a portion of a human occiput. As shown, first section 150 includes pre-auricular extension 420, adjacent mastoid support 402, providing recesses for allowing the subject's ears to reside outside of the device. As shown, second section 160 includes: occiput aperture 427 for drainage positioned posteriorly within occiput rim 401 optionally surrounded by absorbent fabric 426.

Still referencing FIGS. 4A-C, the plurality of pneumatic pillars 406, and 417, provide for openings 431, with the advantage of reducing the overall weight of the device, cost of manufacture, and providing ample air circulation during use. In addition, a pair of pneumatic pillars 417 provide a curved aperture 413, where curved aperture 413 provides for a surgical airway without necessitating the removal of the device. In one example, one or more sets fasteners 411, attached to adjacent inflatable pillars are provided for securing the pillars in spaced apart positions in a releasable manner. In addition, a pair of pneumatic pillars 417 provide a curved aperture 413, where curved aperture 413 provides for a surgical airway to subject without necessitating the removal of the device.

Figure 5A:
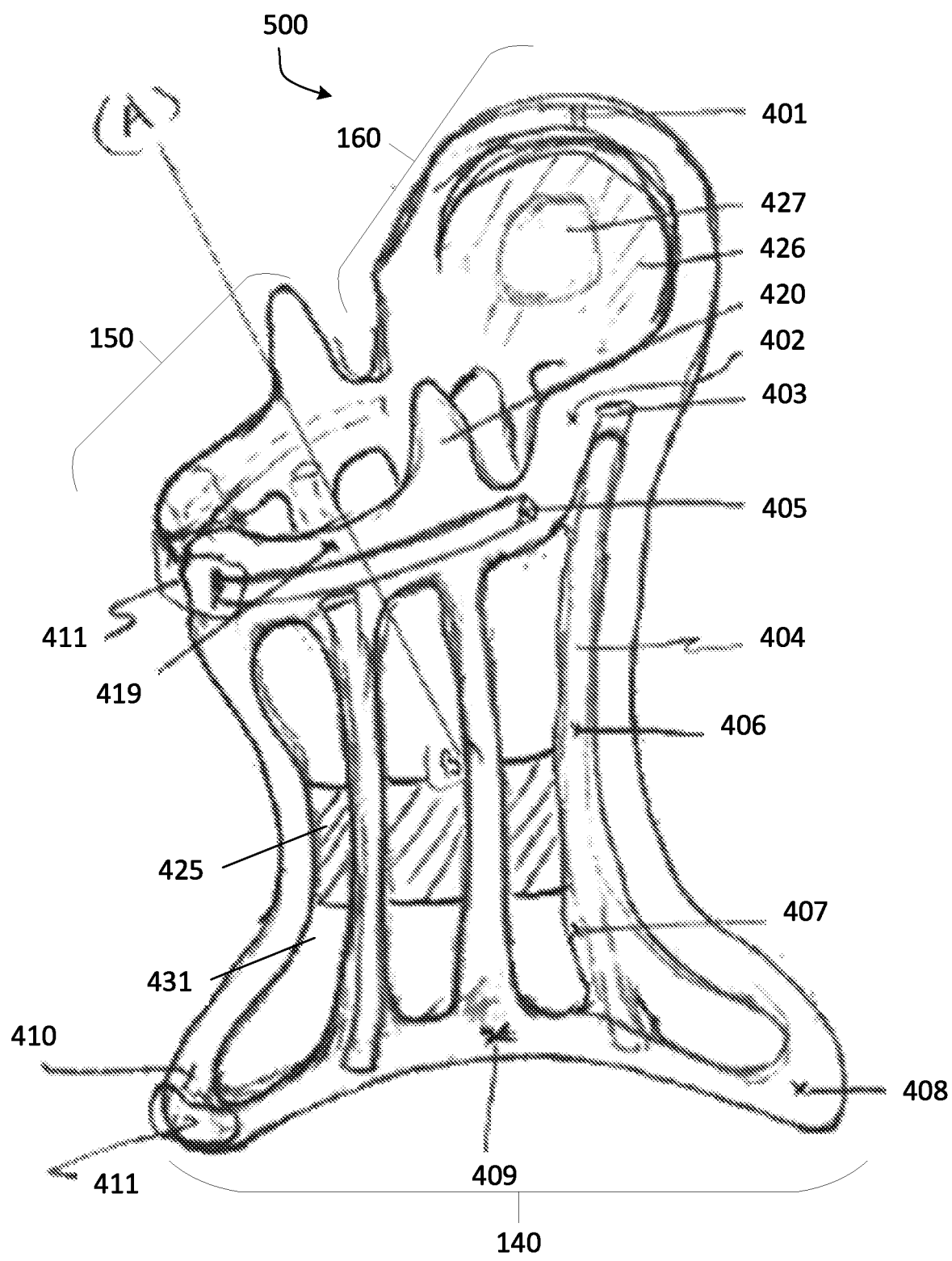
FIGS. 5A and 5B are partial lateral and anterior perspective views, respectively, of an alternate embodiment of the device disclosed and described herein.
Figure 5B:
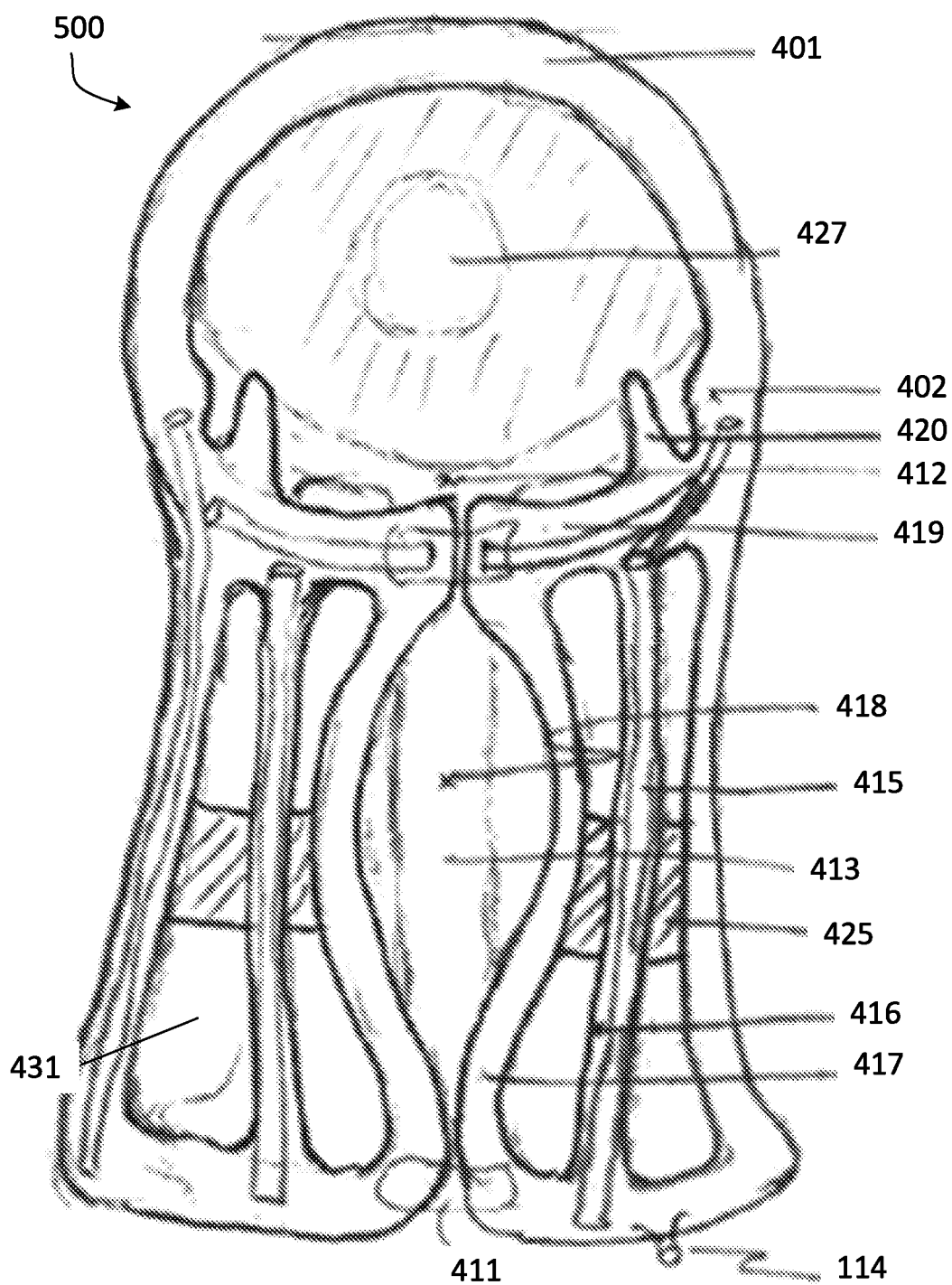

With reference to FIGS. 5A and 5B, another exemplary additional embodiment of the present disclosure is shown as device 500. Device 500 also comprises a generally tubular structure, having a longitudinal axis A-B, the tubular structure comprising a ring-shaped pneumatic bottom portion 140; a ring-shaped pneumatic top portion having a first section 150 and a second section 160 extending from the first section as previously described for device 100.

Device 500 further comprises, horizontal stabilizing members 425 positioned between at least two of the plurality of pneumatic pillars 406, 412, the horizontal stabilizing members 425 spanning openings 431, with the advantage of providing additional axial stability to the pneumatic pillars reducing the overall weight of the device, cost of manufacture, and providing ample air circulation during use.

The device as disclosed and described can be manufactured in a number of ways familiar with those of skill in the art, such as preparing a sheet form which is folded and bonded along a seam. The device can also be injection molded or reaction injection molded or can be constructed in a manner similar to that used for glove manufacture (dip forming) with seam-sealing.

While the disclosure has been illustrated and described as embodied in a multi-chambered, pneumatic cervical collar device, it is not intended to be limited to the details shown, since it will be understood that various omissions, modifications, substitutions and changes in the forms and details of the formulation illustrated and in its operation can be made by those skilled in the art without departing in any way from the spirit of the present disclosure.

The invention claimed is:

1. A collar device comprising:
   a tubular structure having a longitudinal axis, the tubular structure comprising:
   a pneumatic bottom portion configured for contouring with human shoulders;
   a pneumatic top portion having an anterior first section configured to receive and engage a human mandible, and a posterior second section, the posterior second section extending from the anterior first section, the pneumatic top portion terminating as a posterior occiput rim, the posterior second section in combination with the posterior occiput rim being configured to receive entirely a posterior of a human occiput; and
   a plurality of inflatable pillars each generally aligned with the longitudinal axis of the tubular structure, the plurality of inflatable pillars each having a proximal end in proximity to the bottom portion and each having a distal end in proximity to the anterior first section and the posterior second section of the top portion.

2. The collar device of claim 1, wherein the pneumatic top portion has a generally hollow cylindrical shape, the first section configured for contouring with at least a portion of a human mandible, the second section comprising an occiput cushion positioned posteriorly between the occiput rim and the first section configured for cushioning at least a portion of a posterior human occiput.

3. The collar device of claim 1, wherein the top portion further comprises at least 1 of:
   a mastoid support section; and a pre-auricular extension.

4. The collar device of claim 1, further comprising at least one strut aligned with, and contained within or adjacent to, one of the plurality of inflatable pillars.

5. The collar device of claim 4, further comprising at least one mandibular strut, contained within or adjacent to, the anterior first section.

6. The collar device of claim 4, wherein the at least one strut is of a flexibly rigid material.

7. The collar device of claim 1, wherein the tubular structure comprises fasteners for reversibly opening and closing the tubular structure.

8. The collar device of claim 7, wherein the fasteners are aligned along the longitudinal axis and provide for separation of the anterior first section together with a portion of the pneumatic bottom section.

9. The collar device of claim 1, wherein the pneumatic bottom portion and the pneumatic top portion are operably connected to an inflation device, optionally having a pressure relief valve.

10. The collar device of claim 1, further comprising at least one horizontal stabilizing member positioned between the pneumatic bottom portion and the pneumatic top portion, the horizontal stabilizing member connected to at least two of the plurality of inflatable pillars.

11. A collar device comprising:
    a tubular structure having a longitudinal axis, the tubular structure comprising:
    a ring-shaped pneumatic bottom portion configured for contouring with at least a portion of human shoulders;
    a ring-shaped pneumatic top portion having an anterior first section configured for contouring with at least a portion of a human mandible and a posterior second section extending from the anterior first section, the ring-shaped pneumatic top portion terminating with a posterior occiput rim, the posterior second section in combination with the occiput rim being configured for contouring with and receiving entirely a posterior human occiput; and
    a plurality of inflatable struts each generally aligned with the longitudinal axis of the tubular structure, the plurality of struts each having a proximal end in proximity to the bottom portion and each having a distal end in proximity to the anterior first section, the posterior second section, or the posterior occiput rim of the top portion.

12. A method of stabilizing the cervical area of a subject in need thereof, the method comprising:
    securing to a cervical area of a subject a tubular structure having a longitudinal axis, the tubular structure comprising:
    a pneumatic bottom portion configured for contouring with human shoulders;
    a pneumatic top portion having an anterior first section and a posterior second section extending from the first section, the pneumatic top portion terminating as a posterior occiput rim, the posterior second section in combination with the posterior occiput rim receiving entirely and securing a posterior occiput; and
    a plurality of inflatable struts each generally aligned with the longitudinal axis of the tubular structure and that of a head and shoulders of a human, the plurality of struts each having a proximal end in proximity to the bottom portion and each having a distal end in proximity to either one of the anterior first section or the posterior second section of the top portion; and
    at least partially inflating the inflatable struts and one or both of the bottom portion and the top portion.

13. The method of claim 12, wherein the step of at least partially inflating one or both of the bottom portion and the top portion reduces or eliminates extension, flexion, rotation, and traction of the cervical area.

\* \* \* \* \*